US011234904B2

(12) United States Patent
Utterodt et al.

(10) Patent No.: US 11,234,904 B2
(45) Date of Patent: Feb. 1, 2022

(54) DENTAL COMPOSITE MATERIAL AND MILL BLANKS CONSISTING OF SAID COMPOSITE MATERIAL

(71) Applicant: KULZER GMBH, Hanau (DE)

(72) Inventors: Andreas Utterodt, Neu-Anspach (DE); Kurt Reischl, Merenberg (DE); Nelli Schönhof, Braunfels (DE); Michael Eck, Schmitten (DE); Raif Kocoglu, Grävenwiesbach (DE); Jutta Schneider, Runkel (DE); Caroline Kempka, Wölfersheim (DE)

(73) Assignee: KULZER GMBH, Hanau (DE)

( * ) Notice: Subject to any disclaimer, the term of this patent is extended or adjusted under 35 U.S.C. 154(b) by 0 days.

(21) Appl. No.: 16/753,469

(22) PCT Filed: Oct. 1, 2018

(86) PCT No.: PCT/EP2018/076594

§ 371 (c)(1),
(2) Date: Apr. 3, 2020

(87) PCT Pub. No.: WO2019/068614

PCT Pub. Date: Apr. 11, 2019

(65) Prior Publication Data

US 2020/0315925 A1 Oct. 8, 2020

(30) Foreign Application Priority Data

Oct. 4, 2017 (DE) ..................... 10 2017 123 016.5

(51) Int. Cl.

| | |
|---|---|
| ***A61K 6/891*** | (2020.01) |
| ***A61K 6/77*** | (2020.01) |
| ***A61K 6/887*** | (2020.01) |
| ***A61K 6/84*** | (2020.01) |
| ***A61K 6/78*** | (2020.01) |
| ***A61K 6/818*** | (2020.01) |
| ***A61K 6/893*** | (2020.01) |
| ***A61K 6/17*** | (2020.01) |
| ***C08K 3/22*** | (2006.01) |
| ***C08K 3/40*** | (2006.01) |

(52) U.S. Cl.

CPC ................ *A61K 6/891* (2020.01); *A61K 6/17* (2020.01); *A61K 6/77* (2020.01); *A61K 6/78* (2020.01); *A61K 6/818* (2020.01); *A61K 6/84* (2020.01); *A61K 6/887* (2020.01); *A61K 6/893* (2020.01); *C08K 3/22* (2013.01); *C08K 3/40* (2013.01); *C08K 2003/2241* (2013.01)

(58) Field of Classification Search

CPC ..................................................... A61K 6/887
See application file for complete search history.

(56) References Cited

U.S. PATENT DOCUMENTS

| | | | | |
|---|---|---|---|---|
| 9,023,916 | B2 | 5/2015 | Blomker et al. | |
| 2002/0082315 | A1 * | 6/2002 | Moszner ................ | A61K 6/893 523/106 |
| 2012/0082958 | A1 | 4/2012 | Blomker et al. | |

FOREIGN PATENT DOCUMENTS

| | | | |
|---|---|---|---|
| EP | 2 436 365 | A2 | 4/2012 |
| EP | 3 135 270 | A1 | 3/2017 |
| EP | 3 278 787 | A1 | 2/2018 |
| WO | 2016/159219 | A1 | 10/2016 |

OTHER PUBLICATIONS

Watanabe, Takeshi, J. Fukuoka Dent. Coll. 19 (1), pp. 11-24, 1992.

* cited by examiner

*Primary Examiner* — Michael F Pepitone
(74) *Attorney, Agent, or Firm* — Norris McLaughlin, P.A.

(57) ABSTRACT

A polymerisable dental composite material comprising
(i) 70 to 85% by weight of an inorganic filler component comprising at least one dental glass and optionally at least one amorphous metal oxide,
(ii) 10 to 30% by weight of at least one monomer comprising 1,3-bis(5'-alkyl-3',8'-dioxo-2'-aza-4',7'-dioxa-decyl-9'-en) phenyl and/or 1,3-bis(5',9'-dialkyl-3',8'-dioxo-2'-aza-4',7'-dioxa-decyl-9'-en)phenyl,
(iii) 0.01 to 5% by weight of at least one di-, tri-, tetra- or multi-functional monomer not being a urethane (meth) acrylate,
(iv) 0.01 to 10% by weight of at least one initiator, of an initiator system and optionally of at least one stabilizer and optionally of at least one pigment, wherein the total composition of the composite material amounts to 100% by weight, and a polymerized composite material having a flexural strength of greater than or equal to 190 MPa and an elastic modulus of 12 to 21 GPa for the production of indirect dentures.

19 Claims, No Drawings

DENTAL COMPOSITE MATERIAL AND MILL BLANKS CONSISTING OF SAID COMPOSITE MATERIAL

This application is a 371 of PCT/EP2018/076594, filed Oct. 1, 2018, which claims foreign priority benefit under 35 U.S.C. § 119 of the German Patent Application No. 10 2017 123 016.5, filed Oct. 4, 2017, the disclosures of which are incorporated herein by reference.

The invention relates to a polymerisable dental composite material, comprising (i) 60 to 85% by weight of at least one inorganic filler component comprising at least one dental glass as well as optionally at least one amorphous metal oxide, (ii) 10 to 40% by weight of at least one monomer comprising 1,3-bis (5'-alkyl-3',8'-dioxo-2'-aza-4',7'-dioxa-decyl-9'-en)phenyl and/or 1,3-bis(5',9'-dialkyl-3',8'-dioxo-2'-aza-4',7'-dioxa-decyl-9'-en)phenyl, wherein the alkyl groups, each independently, are selected from linear or branched C1 to C4 alkyl groups, optionally in a mixture of at least two different urethane (meth)acrylates, (iii) 0.01 to 5% by weight of at least one di-, tri-, tetra- or multi-functional monomer not being a urethane (meth)acrylate, and (iv) 0.01 to 10% by weight of at least one initiator, of an initiator system as well as optionally stabilizers and optionally of at least one pigment, wherein the total composition of the composite material amounts to 100% by weight, as well as a polymerized composite material having a flexural strength of greater than or equal to 190 MPa and an elastic modulus of 12 to 21 GPa.

Many dental composites universally usable for a direct adhesive restoration as well as for the extraoral fabrication of indirect dentures are known. From the material class of dental composites, only inorganic-organic hybrid materials with larger amounts of inorganic filling materials such as e.g. dental glass and/or mineral nano agglomerates are suitable. Micro filler composites with pre-polymer fillers introduced in the 1980s are not suitable for use in the posterior region (classes I and II) due to the limited wear resistance (abrasion resistance).

A high filler content is advantageous in order to achieve very good mechanical properties of the cured composite and to reduce the polymerization shrinkage that occurs during curing at the same time. These properties are also decisive for the long-term success of the denture material.

The excellent material properties of dental composites with polyalicyclic structural elements for direct adhesive restoration, especially the low shrinkage force and high flexural strength, are well known.

It was the object of the invention to provide a dental composite material being suitable for the production of larger blocks of material, in particular of geometric moulded bodies such as milling blocks. In addition, the object was to provide a dental composite material having a homogeneous, monochrome coloring before and after polymerization. In this context, the homogeneous, monochrome coloring should also be feasible with larger blocks of material. Furthermore, polychrome, i.e. multi-colored blocks of material with a defined coloring should be producible. Moreover, a dental composite material should be provided that is easily flowable in the non-polymerized state and yet has excellent mechanical properties in the polymerized state and has low shrinkage during polymerization, even when producing larger blocks of material. Furthermore, the composite material should not develop cracks or pores during curing, even with large-volume blocks of material.

Starting from state-of-the-art composites based on urethane derivatives, the filler system, the monomer mixture as well as the pigment system had to be modified. Like this, the monomer system should be modified in accordance with filler system to obtain an adjusted high flexural strength in combination with an elastic modulus in the range of 12 to 23 GPa for polymerized dental blocks of material of the composite material.

Voluminous moulded parts for the production of larger blocks of material cannot be photo-polymerized due to the limited penetration depth of the light into the composite material. For this reason, the initiator system had to be adapted and further developed by using at least one thermally initiatable peroxide. In addition, it was necessary to avoid discolorations of existing photoinitiators due to thermal reactions or the significantly increased material dimension in the blocks of material. Therefore, usual blue light photoinitiators, such as the camphorquinone initiator system, were excluded in order to avoid color changes due to the composite layer thickness. When choosing the initiator system, care must be taken that, on the one hand, no stresses are built up in the large blocks of material due to the reaction kinetics, for example of a peroxide, in order to avoid cracking in the interior of the blocks, since the thermal conductivity of the materials is low.

Moulding for the production of the blocks of material is carried out by inserting the polymerizable dental composite material into a casting mould, hereinafter only referred to as mould, under pressure. The applied pressure is preferably between 500 and 300 MPa or [N/mm2]. Polymerization is performed at elevated temperature, preferably being in the range of about 90 to 150° C. The polymerization is carried out at a pressure of about 90 to 300 MPa or [N/mm2]. It is polymerized in a closed casting mould to minimize, preferably avoid, the formation of air bubbles. Preferably, it is polymerized under a pressure of 120 to 320 MPa, preferably to less than or equal to 300 MPa, at a temperature of 100 to 180° C., preferably about 140° C., for at least 10 minutes to 10 hours. The blocks of material preferably have a dimension of at least 1 cm in all special directions and are present as geometric moulded bodies.

Surprisingly, it has been found that composites based on a urethane monomer having an aromatic structural element, such as bis-functionalised phenyl derivatives, are extremely well suited for the production of indirect dentures, since surprisingly high flexural strengths in combination with high elastic modules in the range of the natural hard tooth tissue may be achieved by thermally initiated polymerization. The high level of polymer strength compared to the already described photopolymerization in the case of light-curing dental composites was surprising and not to be expected with these significantly increased values. At the same time, the low-shrinkage crosslinking of the relatively large amount of composite in one process step is advantageous in order to avoid stress cracks in the block/blank. High crosslinking densities being desirable for material strength can often result in unusability of the polymerized molded parts due to the high shrinkage stresses.

A subject matter of the invention is a polymerisable dental composite material, in particular a thermally polymerisable composite material, comprising (i) 60 to 85% by weight of at least one inorganic filler component comprising at least one dental glass or a mixture of average particle size fraction of dental glasses, as well as optionally at least one amorphous metal oxide, (ii) 10 to 40% by weight of at least one monomer comprising 1,3-bis(5'-alkyl-3',8'-dioxo-2'-aza-4',7'-dioxadecyl-9'-en)phenyl and/or 1,3-bis(5',9'-dialkyl-3',8'-dioxo-2'-aza-4',7'-dioxa-decyl-9'-en)phenyl of general formula II, wherein the alkyl groups ($R^1$, $R^2$, $R^3$ and $R^4$), each independently, may be selected from C1 to C4 alkyl groups, in particular from linear or branched non-substituted or substituted alkyl groups, 1,3-bis(5'-methyl-3',8'-dioxo-2'-aza-4',7'-dioxa-decyl-9'-en)phenyl of formula I and/or 1,3-bis(5',9'-dimethyl-3',8'-dioxo-2'-aza-4',7'-dioxa-decyl-9'-en) phenyl are preferred, optionally in a mixture of at least two different urethane (meth)acrylates, preferably a mixture of at least three different urethane (meth)acrylates, in particular of di- to decafunctional urethane (meth)acrylates, (iii) 0.01 to 5% by weight of at least one di-, tri-, tetra- or multi-functional monomer not being a urethane (meth)acrylate, or of a di(meth)acryloyltetrahydrodicyclopentadiene or of a derivative thereof, in particular comprising bis(methacryloyloxymethyl)tetrahydrodicyclo-pentadiene, bis(acryloyloxymethyl)tetrahydrodicyclopentadiene as well as optionally mixtures comprising at least a 3,8-/3,9-/4,8-/3,10-/4,10 isomer and/or cis isomer and trans isomer of the afore-mentioned compounds, in the following referred to as TCD-dimethacrylic esters, and optionally in the mixture with preferably a di-, tri-, tetra- or multi-functional monomer not being a urethane (meth)acrylate, (iv) 0.01 to 10% by weight of at least one initiator, of an initiator system as well as optionally of at least one stabilizer and optionally of at least one pigment, wherein in particular the at least one pigment comprises both at least one fluorescence pigment and color pigment, wherein the total composition of the composite material amounts to 100% by weight.

polymerized composite material is preferably present as block of material, in particular in the form of a milling blank having a dimension of at least 10 cm in all spatial directions.

The following dental glasses are preferably considered: aluminosilicate glasses or fluoroaluminosilicate glasses, barium aluminum silicate, strontium silicate, strontium borosilicate, lithium silicate and/or lithium aluminum silicate as well as mixtures of at least two of the aforementioned dental glasses. Amorphous spherical fillers based on oxide or mixed oxide, such as amorphous $SiO_2$, $ZrO_2$ or mixed oxides of $SiO_2$ and $ZrO_2$, may be used as metal oxide or as a mixture of amorphous metal oxides.

According to a preferred embodiment, the dental composite material comprises at least one dental glass, in particular a radiopaque dental glass, of an average particle size $d_{50}$ of 0.1 to 1.0 μm, in particular in an alternative of 0.7 to 1.0 μm, 0.7 μm to 0.9 μm, preferably having an average particle size of 0.8 to 0.95 μm, in particular with $d_{50}$ of 0.90 μm optionally plus/minus 0.05 μm, preferably plus/minus 0.05 μm, and preferably with $d_{99}$ less than or equal to 10 μm. An average particle size of $d_{50}$ of about 0.85 μm optionally plus/minus 0.1 μm, in particular plus/minus 0.05 μm, particularly preferably plus/minus 0.03 μm, and preferably with $d_{99}$ less than or equal to 10 μm, is particularly preferred. In a further alternative, the average particle size amount to 0.3 to 0.5 μm, in particular with $d_{50}$ of 0.40 μm optionally plus/minus 0.15 μm, preferably plus/minus 0.05 μm, and preferably with $d_{99}$ less than or equal to 10 μm. An average particle size of $d_{50}$ of approximately 0.40 μm optionally plus/minus 0.1 μm, in particular plus/minus 0.05 μm, preferably in particular plus/minus 0.03 μm, and preferably with $d_{99}$ less than or equal to 10 μm, is particularly preferred.

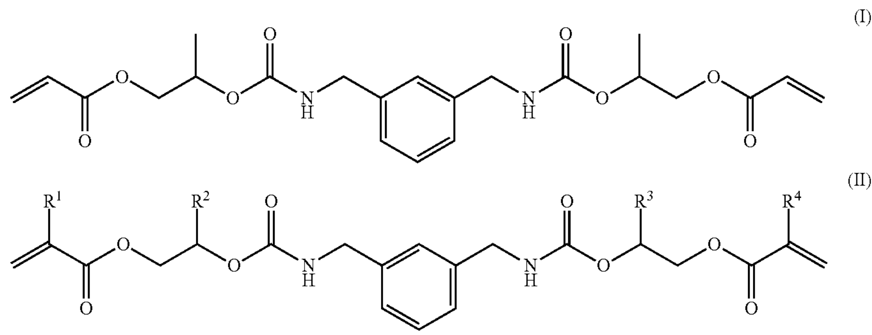

with $R^1$, $R^2$ and $R^3$, $R^4$ equal to, each independently, H or C1-C4 alkyl non-substituted or substituted, in particular with $R^1$, $R^4$ equal to H and $R^2$ and $R^3$ equal to to 4 Alkyl.

In one embodiment variant, it is preferred for the thermally polymerisable composite material to be additionally photochemically polymerisable. A thermally polymerisable composite material is presently understood to mean a composite material that may be polymerized at greater than or equal to 60 to 150° C., preferably at greater than or equal to 70 to 150° C., particularly preferably from 90 to 150° C. In this context, according to the invention it is further preferred for the volume shrinkage to be less than or equal to 1.5%.

By polymerizing the composite material according to the invention, a polymerized composite material having a flexural strength of greater than or equal to 190 MPa, in particular greater than or equal to 230 MPa, and an elastic modulus of 12 to 21 GPa, in particular both dry and also after water storage with thermocycling, is obtainable. The A particularly preferred dental glass comprises barium aluminum borosilicate glass. Moreover, a barium aluminum silicate glass having a reflective index of n=1.52 to 1.55, preferably 1.53, is particularly preferred. A particularly preferred particle size distribution may be in the range of $d_{10}$ with greater than or equal to 0.05 μm to $d_{99}$ less than or equal to 5 μm, preferably with $d_{10}$ greater than or equal to 0.42 μm to $d_{99}$ less than or equal to 2.5 μm and an average diameter $d_{50}$ of 0.4 to 0.9 μm.

According to a preferred embodiment, the dental composite material comprises (i) 70 to 85% by weight of at least one inorganic filler component, comprising at least one dental glass or a mixture of dental glasses having different average particle sizes, wherein the average particle size $d_{50}$ in the range of 0.7 to 1.0 μm is greater than or equal to 70 to 80% by weight, based on the composite material, in particular of greater than or equal to 71 to 76% by weight.

Furthermore, a subject matter of the invention is a dental composite material comprising (i) 60 to 85% by weight of at least one inorganic filler component comprising at least one dental glass comprising barium aluminum borosilicate glass, barium aluminum borfluorosilicate glass, in particular silanised, preferably functionalised with methacryloxypropyl groups, as well as optionally at least one non-agglomerated amorphous metal oxide of a primary particle size of 2 to 45 nm, wherein the amorphous metal oxide comprises precipitated silicon dioxide, zirconium oxide, mixed oxides or mixtures thereof, in particular the metal oxides are silanised.

In order to achieve a high flexural strength, the dental composite material preferably comprises as inorganic filler component (i.1) 70 to 84% by weight of at least one dental glass, in particular 70 to 80% by weight, preferably 71 to 76% by weight, and optionally (i.2) 1 to 15% by weight amorphous metal oxide, in particular 3 to 10% by weight, preferably 4 to 8% by weight, in the total composition. The ratio of dental glass to amorphous metal oxide preferably amounts to 20:1 to 5:1, preferably to 15:1 to 10:1.

According to a particularly preferred embodiment, the dental composite material comprises (i) 60 to 85% by weight of at least one inorganic filler component comprising 60 to 84% by weight, preferably 66 to 76% by weight or 71 to 76% by weight at least one dental glass of an average particle size $d_{50}$ of 0.1 to 0.7 μm, as well as optionally 1 to 25% by weight, preferably 3 to 8% by weight, particularly preferably 5 to 6% by weight at least one amorphous silanised metal oxide of a primary particle size of 2 to 45 nm, based on the total composition, (ii) 10 to 40% by weight, in particular 15 to 30% by weight, preferably 18 to 22% by weight of at least one monomer or a mixture of monomers.

Preferred is a composite material comprising from 10 to 30% by weight, preferably from 115 to 25% by weight at least one monomer selected from 1,3-bis(5'-alkyl-3',8'-dioxo-2'-aza-4',7'-dioxa-decyl-9'-en)phenl and/or 1,3-bis(5',9'-dialkyl-3',8'-dioxo-2'-aza-4',7'-dioxa-decyl-9'-en)phenyl, wherein the alkyl groups, each independently, may be selected from C1 to C4 alkyl groups, in particular alkyl is C1 to C2, 1,3-bis(5'-methyl-3',8'-dioxo-2'-aza-4',7'-dioxa-decyl-9'-en)phenyl of formula I and/or 1,3-bis(5',9'-dimethyl-3',8'-dioxo-2'-aza-4',7'-dioxa-decyl-9'-en)phenyl are preferred, and optionally together with two different urethane (meth)acrylates, in particular of di- to decafunctional urethane (meth)acrylates, preferably from 15 to 19% by weight of a difunctional urethane (meth)acrylate having a bivalent alicyclic group and 5 to 6% by weight of a difunctional urethane (meth)acrylate having a bivalent alkylene group, and optionally 0.1 to 2% by weight of at least one hexafunctional urethane (meth)acrylate or dendritic urethane methacrylate of a mixture of urethane (meth)acrylates, and (iii) 0.01 to 5% by weight, in particular 0.5 to 3% by weight, preferably 0.8 to 2.0% by weight, of at least one di-, tri-, tetra- or multi-functional monomer not being a urethane (meth)acrylate, comprising Bis(methacryloyloxymethyl)tetrahydrodicyclopentadiene, Bis(acryloyloxymethyl)-tetrahydrodicyclopentadiene as well as optionally mixtures comprising at least one 3,8-/3,9-/4,8-/3,10-/4,10 isomer and/or cis isomer and trans isomer of the afore-mentioned compounds optionally in mixture with at least one di-, tri-, tetra- or multi-functional methacrylic ester of polyethers, preferably dimethacrylate triethylene glycol, (iv) 0.01 to 10% by weight, in particular 0.5 to 5% by weight, preferably 0.5 to 2% by weight of at least one thermal initiator, of a thermal initiator system as well as optionally of at least one stabilizer and optionally of at least one pigment, in particular of a pigment mixture comprising a pigment selected from fluorescence pigments and color pigments, wherein the total composition of the composite material amounts to 100% by weight, preferably with filler component to 100% by weight of the composite material.

The di- to decafunctional urethane (meth)acrylates are used as monomers and do not comprise peroxy groups.

According to an embodiment, the dental composite material may comprise a mixture of at least two different urethane (meth)acrylates, preferably of three different urethane (meth)acrylates, selected from at least one difunctional urethane (meth)acrylate having a bivalent alicyclic group, a difunctional urethane (meth)acrylate having a bivalent alkylene group as well as optionally as least one tetrafunctional dendritic urethane (meth)acrylate, preferably at least one hexafunctional dendritic urethane (meth)acrylate. Particularly preferred difunctional urethane (meth)acrylates having a bivalent alicyclic group comprise bis(4',7'-dioxa-3',8'-dioxo-2'-aza-decyl-9'-en)tetrahydrodicyclopentadiene, bis(4',7'-dioxa-3',8'-dioxo-2'-aza-9'-methyl-decyl-9'-en)tetrahydrodicyclopentadiene and/or mixtures thereof, as well as optionally mixtures of the 3,8-/3,9-/4,8-/3,10-/4,10 isomers and/or of the cis isomers and trans isomers of the afore-mentioned compounds.

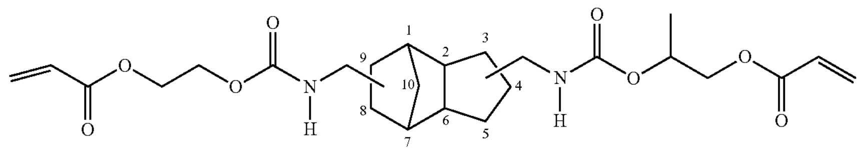

The difunctional urethane (meth)acrylate having a bivalent alicyclic group is preferably selected from linear or branched urethane dimethacrylates being functionalised with a bivalent alkylene group, urethane dimethacrylate-functionalised polyethers having alkylene group(s), such as bis(methacryloxy-2-ethoxycarbonylamino)alkylene, bis (methacryloxy-2-ethoxycarbonylamino)-substituted polyalkylene ethers, preferably 1,6-bis(methacryloxy-2-ethoxycarbonylamino)-2,4,4-trimethylhexane, UDMA or HEMA-TDMI. A bis(methacryloxy-2-ethoxycarbonylamino) alkylene, wherein alkylene comprises linear or branched C3 to C20, preferably C3 to C6, is preferred, such as, particularly preferably, an alkylene substituted with methyl groups, such as HEMA-TMDI. The bivalent alkylene preferably comprises 2,2,4-trimethylhexamethylene and/or 2,4,4-trimethylhexymethylene.

The at least tetrafunctional dendritic urethane methacrylate comprises tetra- to decafunctional dendritic urethane methacrylates.

According to a further preferred embodiment, the dental composite material comprises as component (iii) 0.01 to 5% by weight of at least one di-, tri-, tetra- or multi-functional monomer not being a urethane acrylate and being selected from (meth)acrylic esters of tetrahydrodicyclopentadiene, preferably bis(methacryloyloxymethyl)tetrahydrodicyclopentadiene, bis(acryloyloxymethyl)tetrahydrodicyclopentadiene, di(meth)acrylic esters as well as mixture comprising at least one 3,8-/3,9-/4,8-/3,10-/4,10 isomer and/or cis isomer and trans isomer of the afore-mentioned compounds, and optionally dimethacrylic esters of polyethers, tri-, tetra- or multi-functional methacrylic esters of polyethers. Preferably, the content of components (iii) amounts to 0.15 to 5% by weight, particularly preferably 1.0 to 2% by weight, of a dimethacrylic ester, dimethacrylic ester of a polyether, such as preferably a dimethacrylate polyethylene glycol, dimethacrylate polypropylene glycol. Dimethacrylate triethylene glycol (TEGDMA), diethylene glycol dimethacrylate (DEGMA) and dimethacrylate tetraethylene glycol (TEDMA) are particularly preferred.

Water as stabilizer was added to the dental composite material to improve the consistency and the flow properties for the process-engineering processability. Stabilizers were added to the composite material to prevent premature polymerization and give the material a certain shelf life. The composite material comprises as preferred stabilizers in component (iv) at least one stabilizer selected from water, at least one benzophenone derivative, preferably alkoxy-substituted benzophenone and/or phenol derivative, such as 2-hydroxy-4-methoxybenzophenone, 2,6-bis(1,1-dimethyl)-4-methylphenol, or a mixture of the three stabilizers. The stabilizers are preferably present in 0.01 to 14% by weight in the total composition, particularly preferably form 0.7 to 10% by weight, in particular from 0.5 to 2% by weight. In addition, it is preferred for the composite material to contain 0.01 to 2% by weight water as stabilizer, preferably 0.1 to 1.0% by weight water.

At least one pigment comprising at least one fluorescence pigment and optionally at least one organic color pigment and/or at least one inorganic color pigment, in particular non-fluorescent color pigments, are added to the composite material for optimal adjustment of the color and natural aesthetic of the polymerized composite material. The at least one fluorescence pigment preferably is an organic fluorescence pigment, in particular a non-polymerisable organic fluorescence pigment, where appropriate comprising aryl carboxylic acid esters, aryl carboxylic acids, coumarin, rhodamine, naphthalene imide or a derivative of the respective substance. Inorganic fluorescence pigments may comprise $CaAl_4O_7:Mn^{2+}$, $(Ba0.98Eu0.02)MgAl_{10}O_{17}$, $BaMgF_4:Eu^{2+}$, $Y(1.995)Ce(0.005)SiO_5$.

The composite may comprise as pigments, in particular colour pigments, organic pigments as well as inorganic pigments, in particular comprising diethyl-2,5-dihydroxy terephthalate, N,N'-Bis(3,5-xylyl)perylene-3,4:9,10-bis(dicarbimide), copper phthalocyanine, titanate pigment, in particular chromium antimony titanate (rutile structure), spinel black, in particular pigments being based on iron oxide black ($Fe_3O_4$), wherein iron (Fe) is partially substituted by chromium and copper or nickel and chromium or manganese, zinc iron chromium spinel, brown spinel, ($(Zn,Fe)(Fe,Cr)_2O_4$), cobalt zinc aluminate blue spinel and/or titanium oxide. The pigments comprising fluorescence pigments and color pigments preferably present in 0.01 to 10% by weight in the total composition, particularly preferably from 0.01 to 5% by weight, preferably from 0.01 to 1% by weight.

Selection of pigments has to be specifically adapted to the dental composite composition in order to achieve a homogeneous color in both the polymerisable composite and the polymerized composite. Also the production of large blocks of material requires coordination with regard to the selection and to the concentration of the pigments in order to avoid undesirable discolorations due to the dimensioning of the polymerized blocks of material.

Peroxides, hydroxyl peroxides or mixtures comprising them are suitable as initiators. Suitable thermal initiators may be used as radical initiators in the temperature range of 70 to 150° Cm preferably of 90 to 150° C. Preferred thermal initiators comprise at least one initiator selected from: tert.-butylperoxy-2-ethylhexanoate, dibenzoylperoxide, dicumylperoxide, dicumyl-hydroperoxide, azobisisobutyronitrile, benzylbarbituric acid derivative.

Another subject matter of the invention is a polymerized dental composite material, in particular a thermally polymerized composite material, obtainable by polymerization of the composite material according to the invention, in particular by polymerization of the composite material at a pressure of 500 to 300 MPa (=[N/mm$^2$]), in particular at 50 to 300 MPa, preferably at 100 to 300 MPa, particularly preferably at 120 to 200 MPa, preferably at 120 to 170 MPa, and/or elevated temperature, preferably at 90 to 150° C. Polymerization is preferably carried out in a casting mould, preferably having a geometric shape. The polymerization under elevated pressure minimizes or avoids air bubble formation in the polymerized composite material.

The shrinkage of the polymerisable composite material preferably amounts to less than or equal to 2.0%, in particular less than 1.5%, particularly preferably less than or equal to 1.4% ((Bonded-Disc method—Dental Materials, Watts et al, (2004) 20, 88-95; 23° C., Translux Energy, 60 s exposure).

The polymerized composite material preferably has no blowholes or cracks of a size of greater than or equal to 200 nm, in particular a block of material has no blowholes or cracks. The polymerized composite material has a density of greater than or equal to 2.0 g/cm$^3$, in particular a density of greater than or equal to 2.1 g/cm$^3$.

Surprisingly, the polymerized dental composite material, in particular being obtainable by thermal polymerization of the composite material, has a flexural strength of greater than or equal to 200 MPa, in particular a flexural strength of greater than or equal to 210 MPa, preferably greater than or equal to 220 MPa, preferably greater than or equal to 230 MPa, greater than or equal to 240 MPa, greater than or equal to 250 MPa according to EN ISO 6872:2008. The flexural strength of the composite material (test specimens dry, dry after polymerization or 7 days, dry 23° C.+/−3° C.) is preferably greater than or equal to 230 MPa, preferably greater than or equal to 240 MPa, greater than or equal to 250 MPa, in particular to less than or equal to 300 MPa. The flexural strength after water storage preferably is greater than or equal to 200 MPa, in particular greater than or equal to 210 MPa, preferably greater than or equal to 220 MPa, in particular greater than or equal to 230 MPa (7 days, 37° C. $H_2O$) according to EN ISO 6872:2008. The flexural strength after 7 days of storage in water with thermocycling is preferably greater than or equal to 200 MPa, preferably greater than or equal to 210 MPa, preferably greater than or equal to 220 MPa, particularly preferably greater than or equal to 230 MPa to less than or equal to 300 MPa according to EN ISO 6872:2008, whereby storage in water was performed analogously to Dent. Matter J. 2014; 33(5) 705-710 with 5000 cycles. The flexural strength and the elastic modulus were prepared and measured (dry as well as after 7 days of storage in water with and without thermocycling)

according to Dent. Materials J 2014; 33(4/5), 705 to 710, i.e. according to EN ISO 6872:2008 or with additional water storage.

The ISO 6872 standard was developed for testing ceramic materials being available as CAD/CAM blocks. Since the composite materials are also produced and machined in the same dimensioning, a comparable analogous test with water storage should be carried out. The production of test specimens according to the composite standard (ISO4049) cannot be carried out from those blocks due to the dimensions of the test specimens.

While the flexural strength of a dental composite is not limited to high values, (>100 MPa), a balanced/optimal elasticity is advantageous for the application. The elastic modulus should ideally correspond to that of the dentin of the hard tooth tissue so that failure in the intended application is avoided as far as possible. Materials that are too brittle (having a high e-modulus) tend to chipping or fracture. Materials that are too elastic (low e-modulus) deform under chewing load and the cementation detaches (debonding).

The material properties (flexural strength and e-modulus) of human hard tooth tissue are known from literature (Dwayne D. Arola et al. Biomaterials 27(2006) 2131-2140) as a function of orientation (anisotropic material properties due to crystal orientation). There, the elastic modulus of human hard tooth structure is between 15 to 19 GPa, depending on the orientation. The aim was therefore to provide a composite having an e-modulus (elastic modulus) being in the range of human hard tooth tissue, thus preferably in the range of 15-20 GPa, to mimic toothlike properties.

Thus, another subject matter of the invention is a polymerized dental composite material having an elastic modulus of greater than or equal to 12 to 21 GPa, preferably from 15 to 20 GPa (dry as well as after 7 days of storage, dry) according to EN ISO 6872:2008, in particular analogously to the method as disclosed in Dent. Mater. J. 2014; 33(5) 705-710. The publication compares in Table 3 further results of the three-point bending flexural test for CAD/CAM blocks of different dental materials.

Preferably, the elastic modulus according to the invention is 12 to 20 GPa, preferably from 14 to 20 GPa, particularly preferably 15 to 20 GPa (measured after 7 days of storage in water with thermocycling) and/or the elastic modulus preferably amounts to greater than or equal to 12 to 20 GPa (7 days, 37° C. $H_2O$), preferably greater than or equal to 14 to 20 GPa, particularly preferably 15 to 20 GPa.

The method in the execution examples is inspired by the method as disclosed in Dent. Mater. J. 2014; 33(5) 705-710. It is clear that setting an e-modulus analogous to that of the hard tooth tissue in the range of 15 to 20 GPa at both dry storage and also a storage at 37° C. plus thermocycling had not been possible so far.

TABLE 1

Flexural strength in MPa and e-modulus in GPa of Table 3 in Dent. Mater. J. 2014; 33(5) 705-710

| | Condition | Block HC | Cera-smart | Gradia Block | Lava Ultimate | Vita Enamic | Vita-blocs Mark II |
|---|---|---|---|---|---|---|---|
| flexural | dry | 170.5 | 242.0 | 204.0 | 170.5 | 140.7 | 126.6 |
| strength | water | 121.5 | 197.3 | 188.4 | 141.9 | 133.0 | 121.1 |
| [MPa] | water/TC | 117.6 | 194.3 | 165.1 | 120.1 | 134.6 | 129.0 |
| e- | dry | 9.6 | 10.0 | 14.7 | 14.5 | 28.5 | 51.5 |

TABLE 1-continued

Flexural strength in MPa and e-modulus in GPa of Table 3 in Dent. Mater. J. 2014; 33(5) 705-710

| | Condition | Block HC | Cera-smart | Gradia Block | Lava Ultimate | Vita Enamic | Vita-blocs Mark II |
|---|---|---|---|---|---|---|---|
| modulus | water | 7.8 | 9.0 | 13.5 | 12.8 | 28.3 | 52.8 |
| [GPa] | water/TC | 7.2 | 8.7 | 13.2 | 12.2 | 28.6 | 54.9 |

According to a particularly preferred embodiment, a subject matter of the invention is polymerized dental composite material comprising 60 to 85% by weight of at least one inorganic filler component comprising at least one dental glass of an average particle size $d_{50}$ of 0.1 to 1.0 μm, as well as optionally at least one amorphous silanised metal oxide of a primary particle size of 2 to 45 nm, 10 to 30% by weight of at least one polymer being based on at least one monomer, preferably being based on a mixture of the following monomers, comprising at least one bis-urethane derivative selected from 3-bis(5'-alkyl-3',8'-dioxo-2'-aza-4',7'-dioxa-decyl-9'-en)phenyl and/or 1,3-bis(5',9'-dialkyl-3',8'-dioxo-2'-aza-4',7'-dioxa-decyl-9'-en)phenyl, wherein the alkyl groups, each independently, are selected from C1 to C4 alkyl groups, optionally in mixture with a difunctional urethane (meth)acrylate of tetrahydrodicyclopentadiene and/or at least one diurethane (meth)acrylate having a bivalent alkylene group and/or at least one tetra- to decafunctional dendritic urethane methacrylate, and at least one di-, tri-, tetra- or multi-functional methacrylic ester comprising bis (methacryloyloxymethyl)tetrahydrodicyclopentadiene, bis (acryloyloxymethyl)tetrahydrodicyclopentadiene, as well as optionally mixtures comprising at least one 3,8-/3,9-/4,8-/3,10-/4,10 isomer and/or cis isomer and trans isomer of the afore-mentioned compounds, as well as optionally in mixture with di-, tri-, tetra- or multifunctional (meth)acrylic esters of polyethers, preferably dimethacrylate triethylene glycol, and 0.01 to 10% by weight of at least one pigment, in particular of at least one fluorescence pigment and of at least one organic color pigment and/or of at least one inorganic color pigment, wherein the color pigments preferably do bot fluoresce, wherein the total composition of the composite material amounts to 100% by weight.

The polymerized dental composite material may preferably be present in the form of a block of material, in particular as three-dimensional block of material in the form of a geometric moulded body, in particular in the form of a milling blank with an adapter for fastening in an automated device to remove material, particularly preferably in the form of a cylinder, of a cuboid, preferably in the form of a cube. In addition, it is preferred for the edges and/or vertices of the moulded body to be rounded. The dimensions of the cylinder preferably amounts to: height of greater than or equal to 10 mm to less than or equal to 15 mm and radius of greater than or equal to 3 to less than or equal to 7 mm, alternatively with a height of greater than or equal to 10 mm to less than or equal to 20 mm and a radius of greater than or equal to 5 to less than or equal to 7 mm. The dimensions of the cuboid preferably amounts to a, b, and c greater than or equal to 4 mm, in particular greater than or equal to 10 mm and a less than or equal to 20 mm, in particular less than or equal to 18 mm, b less than or equal to 14 mm and c less than or equal to 20 mm, in particular less than or equal to 18 mm. Preferably, a three-dimensional block of material as at least an edge length of at least 10 mm each, preferably of 14 mm. Blocks of material being us as milling blanks preferably have the shape of cuboids, wherein the cuboids preferably have a volume of 12 mm×14 mm×17 or 18 mm, alternatively of 14×14 mm, or 15×15 mm as well as a height of 17 to 18 mm. One to all edges and vertices may be straight or rounded.

Furthermore, a subject matter of the invention is the use of a dental composite material for the production of dental prosthetic restorations, in particular for the production of indirect dentures, in a material-removing process, in particular in a process in which the polymerized composite material is removed by means of milling, cutting, polishing, breaking, chipping and/or drilling, particularly preferably in a process in which the composite material is removed by means of laser energy. A particularly preferred use for the material is the use in a method for the production of dental prosthetic restorations in a material-removing process, in which the material is removed by means of laser energy. The particle size as well as preferably the particle size distribution was specially adapted to a method in which the polymerized composite material is removed by means of laser energy and the prosthetic restorations may be produced.

or for the production of direct adhesive dental restorations. A particular advantage of the dental material according to the invention is that it allows the possibility of a significant process simplification in the production of indirect dentures by the dentist or dental technician carrying out at least one intraoral scan in the patient's mouth and may subsequently use the digital dental information obtained in this way to directly fabricate a prosthetic dental restoration, such as a crown or an inlay, taking into account other device parameters, etc. The dental prosthetic restoration produced may then be inserted at the patient, fixed and, if necessary, slightly reprocessed. For example, an intraoral scan is taken before grinding a tooth to produce a tooth stump for a crown and another intraoral scan of the tooth stump.

Furthermore, the polymerized composite material may be used for the production of dental prosthetic restorations comprising crowns, inlay, onlays, superstructures, artificial teeth, dental bridges, dental bars, spacers, abutments or veneers. The polymerized composite material may additionally be used as composite material for the production of direct adhesive dental restorations.

Additionally, the following are also preferably considered to be urethane (meth)acrylates according to the invention: (ii) at least one urethane (meth)acrylate, in particular a urethane dimethacrylate, preferably a bis(methacryloxy-2-ethoxycabonylamino) alkylene, diurethane acrylate oligomers, alkyl-functional urethane dimethacrylate oligomers, aromatic-functionalised urethane dimethacrylate oligomers, aliphatic unsaturated urethane acrylates, bis(methacryloxy-2-ethoxycarbonylamino)-substituted polyethers, aromatic urethane diacrylate oligomers, aliphatic urethane diacrylate oligomers, aliphatic urethane diacrylates, hexafunctional aliphatic urethane resins, aliphatic urethane triacrylates, aliphatic urethane acrylate oligomers, unsaturated aliphatic urethane acrylates. Difunctional and multi-function urethane (meth)acrylates are preferred, such as, in particular, urethane di(meth)acrylate, the at least one (iii) urethane dimethacrylate is particularly preferably selected from linear or branched alkyl-functionalised urethane dimethacrylates, urethane dimethacrylate-functionalised polyethers, in particular bis(methacryloxy-2-ethoxycarbonylamino)alkylene, bis(methacryloxy-2-ethoxycarbonylamino)-substituted polyethers, preferably 1,6-bis(methacryloxy-2-ethoxycarbonylamino)-2,4,4-trimethylhexane. Suitable urethane (meth) acrylates are available under the following brand names: Ebecryl 230 (aliphatic urethane diacrylate), Actilane 9290, Craynor 9200 (Diurethane acrylate oligomer), Ebecryl 210 (aromatic urethane diacrylate oligomers), Ebecryl 270 (aliphatic urethane diacrylate oligomers), Actilane 165, Actilane 250, Genomer 1122 (monofunctional urethane acrylate), Photomer 6210 (cas no. 52404-33-8, aliphatic urethane diacrylate), Photomer 6623 (hexafunctional aliphatic urethane resin), Photomer 6891 (aliphatic urethane triacrylate), UDMA, Roskydal LS 2258 (aliphatic urethane acrylate oligomer), Roskydal XP 2513 (unsaturated aliphatic urethane acrylate). The urethane (meth)acrylates may preferably be selected from the afore-mentioned urethane (meth) acrylates or from a mixture of at least two different, preferably at least three different, afore-mentioned urethane (meth)acrylates.

The at least one further di-, tri-, tetra- or multi-functional monomer not being urethane (meth)acrylate may preferably be selected from at least one of the following monomers, in particular a mixture of monomers comprising 1,4-butandiol dimethacrylate (1,4-BDMA) or pentaerythritol tetraacrylate, bis-GMA monomer (bisphenol-A-glycidyl methacrylate), triethylene glycol dimethacrylate (TEGDMA) and diethylene glycol dimethacrylate (DEGMA), tetraethylene glycol di(meth)acrylate, decanediol di(meth)acrylate, dodecandiol di(meth)acrylate, hexyldexandiol di(meth)acrylate, trimethylolpropane tri(meth)acrylate, pentaerythritol tetra(meth) acrylate as well as butanediol di(meth)acrylate, ethylene glycol di(meth)acrylate, polyethylene glycol di(meth)acrylate, ethoxylated/propoxylated bisphenol-A-di(meth)acrylate, of a mixture comprising at least one of these (meth) acrylates and/or copolymers comprising one or at least two of the aforementioned monomers.

Typical further difunctional monomers, also referred to as crosslinker and/or multi-crosslinker, include tri- or tetraethylene glycol di(meth)acrylate, BDMA, 1,4-butandiol dimethacrylate (1,4-BDMA), bis-GMA monomer (bisphenol-A-glycidylmethacrylate, an addition product of methacrylic acid and bisphenol-A diglycidylether), diethylene glycol di(meth)acrylate, bisphenol-A di(meth)acrylate, decanediol di(meth)acrylate, dodecandiol di(meth)acrylate, hexyldexandiol di(meth)acrylate as well as butanediol di(meth)acrylate, ethylene glycol di(meth)acrylate, polyethylene glycol di(meth)acrylate, ethoxylated/propoxylated bisphenol-A-di (meth)acrylate. The following difunctional monomers may also be added as diluting agent (low viscosity acrylates). Tri- and tetrafunctional monomers and/or multi-crosslinkers comprise trimethylolpropane tri(meth)acrylate, tris(2-hydroxyethyl)-isocyanurate triacrylate, pentaerythritol tetraacrylate.

At least one of the following monomers may be present in the composite material in addition to the di-, tri- or multi-functional monomer or monomers, comprising at least one monomer, in particular a mixture of monomers of methylmethacrylate, ethylmethacrylate, propylmethacrylate, butylmethacrylate, n-hexylmethacrylate, 2-phenoxyethylmethacrylate, isobornylmethacrylate, isodecylmethacrylate, polypropylene glycol monomethacrylate, tetrahydrofurylmethacrylate, methylacrylate, ethylacrylate, propylacrylate, butylacrylate, n-hexylacrylate, 2-phenoxyethylacrylate, isobornylacrylate, isodecylacrylate, polypropylene glycol monoacrylate, tetrahydrofurylacrylate, hydroxyethylacrylate, hydroxypropylacrylate, hydroxyethylmethacrylate, hydroxypropylmethacrylate, benzyl-, furfuryl- or phenyl (meth)acrylate, a mixture containing at least one of these (meth)acrylates and/or copolymers comprising one or at least two of the aforementioned monomers.

Furthermore, a subject matter of the invention is a composite material comprising, preferably additionally, at least one or more substance(s) from the groups consisting of fillers, pigments, stabilizers, regulators, antimicrobial additives, UV-absorbing agents, thixotroping agents, catalysts and crosslinkers. Rather small amounts of said additives—as also of pigments, stabilizers and regulators—are used, e.g. a total of 0.01 to 3.0% by weight, in particular 0.01 to 1.0% by weight, based on the total mass of the material. Suitable stabilizers include e.g. hydroquinone monomethylether or 2,6-di-tert.-butyl-4-methylphenol (BHT).

The following initiators and/or initiator systems for auto- or cold-polymerization comprise a) at least one initiator, in particular at least one peroxide and/or azo compound, in particular LPO: dilauroylperoxide, BPO: dibenzoylperoxide, t-BPEH: tert.-butyl-peroxy-2-ethylhexanoate, AIBN: 2,2'-azobis-(isobutyronitrile), DTBP: di-tert-butylperoxide, and, optionally, b) at least one activator, in particular at least one aromatic amine, such as N,N-dimethyl-p-toluidine, N,N dihydroxyethyl-p-toluidine and/or p-dimethylaminobenzoic acid diethylester, or c) at least one initiator system selected from redox systems, in particular a combination selected from dibenzoylperoxide, dilauroylperoxide, and camphorquinone with amines selected from N,N dimethyl-p-toluidine, N,N-dihydroxyethyl-p-toluidine, and p-dimethyl-amino-benzoic acid diethylester. The initiator may alternatively be a redox system comprising a peroxide, and a reduction agent selected from ascorbic acid, ascorbic acid derivative, barbituric acid or a barbituric acid derivative, sulfinic acid, sulfinic acid derivative, particularly preferred is a redox system comprising (i) barbituric acid or thiobarbituric acid or a barbituric acid derivative or thiobarbituric acid derivative, and (ii) at least one copper salt or copper complex, and (iii) at least one compound having an ionic halogen atom, particularly preferred is a redox system comprising 1-benzyl-5-phenylbarbituric acid, copper acetylacetonate, and benzyldibutylammonium chloride. Particularly preferably, the polymerization in the two-component prosthetic base material is started by a barbituric acid derivative.

In general, Initiators for the polymerization reaction of cold- or auto-polymerizing starting mixtures are considered to be those with which radical polymerization reactions may be started. Preferred initiators are peroxides as well as azo compounds, such as, for example, the following: LPO: dilauroylperoxide, BPO: dibenzoylperoxide, t-BPEH: tert.-butylperoxi-2-ethylhexanoate, AIBN: 2,2'-azobis-(isobutyronitrile), DTBP: di-tert.-butylperoxide.

In order to accelerate the initiation of radical polymerization by peroxides, suitable activators, e.g. aromatic amines, may be added. Examples of suitable amines are N,N-dimethyl-p-toluidine, N,N-hydroxyethyl-p-toluidine and p-dibenzylaminobenzoic acid diethylester. In this context, the amines regularly function as co-initiators and are usually present in an amount of up to 0.5% by weight.

The below execution examples shall clarify the invention without limiting it to these examples.

EXECUTION EXAMPLES

Three-Point Bending Flexural Test

Flexural properties were determined using a three-point bending flexural test according to ISO 6872:2008 (ISO 6872:2008. Dentistry—Ceramic materials, 3rd ed, International Organization for Standardization, Geneva, 2008). The rod-shaped specimens, 4.0 mm wide, 14.0 mm long and 1.2 mm thick, were produced with a low-speed diamond saw (Isomet, Buehler, Lake Bluff, Ill., USA). All specimens were wet ground and polished with a #600 and #1000 diamond wheel (Maruto, Tokyo, Japan) and #1000 diamond blades (Maruto) mounted on a metallographic lapping machine (Dia-Lap, ML-150P, Maruto) to achieve the required dimensions of 4.0±0.2×14.0±0.2×1.2±0.2 mm. In order to minimize edge breaks in the rod-shaped specimens during the bending test, an edge chamfer, 0.15 mm wide, was incorporated using the lapping machine with a #1000 diamond blade. After polishing, all specimens were stored in a silica gel desiccator for 7 days prior to the bending flexural test. Three groups of ten specimens each were randomly produced from each CAD/CAM block. Specimens of the first group were stored under dry conditions at ambient room temperature (23±2° C.) for 7 days. The second group was stored in 37° C. deionized water for 7 days, while the third group was stored in 37° C. deionized water for 7 days followed by 5000 thermal cycles (thermocycling 5° C. to 55° C., retention time 30 s) using a thermocyclic device (HA-K178, Tokyo Giken Inc., Tokyo, Japan). The width and thickness of each specimen were measured using a digital micrometer (MDC-25M, Mitsutoyo Co., Tokyo, Japan, minimum value: 0.001 mm). A three-point bending flexural test with a support span of 12.0 mm and a traverse speed of 1.0 mm/min was performed at ambient room temperature (23±2° C.) by means of a universal testing machine (AG-X, Shimadzu Corp., Kyoto, Japan). The flexural strength and the flexural modulus were calculated by use of software (TRAPEZIUM X, Shimadzu Corp., Kyoto, Japan). The flexural modulus (E) was calculated according to the following formula:

$$E=FL^3/4bh^3d$$

wherein F represents the load at an appropriate point in the linear part of the spring characteristics, L the support span (12.00 mm), b the width of the specimen, h the thickness of the specimen and d the bending at a load F. The flexural strength (σ) was calculated with the following formula:

$$\sigma=3F_1L/2bh^2$$

wherein $F_1$ represents the maximal load during the bending flexural test.

The hardness test was carried out using a Zwick universal device: The measured values of the specimens according to the invention are in the range of 800 to 850.

In the following, comparative examples of light-curing products Venus Diamond (VD) and Venus Pearl (VP) are measured according to ISO 4049 and ISO 6872 (The exposure was carried out point by point according to the method described in EN ISO 4049:2009 7.11 using a Translux 2Wave (1200 mW/cm$^2$) by means of an exposure time of respectively 20 seconds per exposure point) and compared with Example 1 according to the invention.

TABLE 2

Comparison Ex. 1 with Venus products

| | | Comparative examples | |
|---|---|---|---|
| | Example 1 | Venus Diamond (VD) | Venus Pearl (VP) |
| Flexural strength [MPa] according to EN ISO 6872 (dry) | | 182 MPa | 195 MPa |
| Elastic modulus [GPa] according to EN ISO 6872 (dry) | | 15.6 GPa | 15.8 GPa |

TABLE 2-continued

| Comparison Ex. 1 with Venus products | | | |
|---|---|---|---|
| | | Comparative examples | |
| | Example 1 | Venus Diamond (VD) | Venus Pearl (VP) |
| Flexural strength [MPa] according to EN ISO 4049 (24 h/water) | | 174 MPa | 149 MPa |
| Elastic modulus [GPa] according to EN ISO 4049 (24 h/water) | | 12.0 GPa | 11.4 GPa |

TABLE 3

| Examples 1 to 4: | | | | | | | |
|---|---|---|---|---|---|---|---|
| | average | Example 1 0.4 μm | | Example 2 0.4 μm | | Example 3 and 4 0.85 μm | |
| dental glass | diameter $d_{50}$ | % by weight | g | % by weight | g | % by weight | g |
| dental glass | barium-aluminum-borofluorsilicate glass (silanised) | 74.31 | 74.31 | 74.31 | 74.31 | 73.31 | 73.31 |
| urethane (meth)-acrylates | 1,3-bis(5'-methyl-3',8'-dioxo-2'-aza-4',7'-dioxa-decyl-9'-en)phenyl (formulal I) | 22.76 | 22.76 | 22.77 | 22.77 | 23.63 | 23.63 |
| TCD ester | TCD-dimethyl-diacrylate ester | 1.26 | 1.26 | 1.27 | 1.27 | 1.31 | 1.31 |
| initiator | tert.-butylperoxy-2-ethylhexanoate | 0.36 | 0.36 | 0.36 | 0.36 | 0.40 | 0.40 |
| | 2,4,6-trimethylbenzoylphenylphosphinic acid ethylester | 0.13 | 0.13 | 0.13 | 0.13 | 0.13 | 0.13 |
| | N,N-dimethyl-4-aminobenzoic acid 2-butoxyethyl-ester | 0.07 | 0.07 | 0.07 | 0.07 | 0.08 | 0.08 |
| stabilizer | 2,6-bis(1,1-dimethylethyl)-4-methyl-phenol | 0.03 | 0.03 | 0.03 | 0.03 | 0.03 | 0.03 |
| | glycerin | 0.55 | 0.55 | 0.54 | 0.54 | 0.56 | 0.56 |
| | 2-hydroxy-4-methoxy-benzophenone | 0.16 | 0.16 | 0.16 | 0.16 | 0.17 | 0.17 |
| | 2-(2H-benzo-triazol-2-yl)-6-dodecyl-4-methyl-phenol | 0.10 | 0.10 | 0.10 | 0.10 | 0.11 | 0.11 |
| | water | 0.25 | 0.25 | 0.25 | 0.25 | 0.26 | 0.26 |
| pigments and others | diethyl-2,5-dihydroxy-terephthalate, color pigments, titanium dioxide | 0.02 | 0.02 | 0.01 | 0.01 | 0.01 | 0.01 |

Polymerization: 3 hours at 95° C.

TABLE 4a

| Flexural strengths and e-modulus (according to EN ISO 6872) without storage | | |
|---|---|---|
| | flexural strength | e-modulus |
| Example 1 | 244 MPa | 18.2 GPa |
| Example 2 | 248 MPa | 17.7 GPa |
| Example 3 | 243 MPa | 14.6 GPa |
| Example 4 | 234 MPa | 14.6 GPa |

TABLE 4b

| Flexural strengths and e-modulus (elastic modulus) (according to EN ISO 6872) 7 days RTdry | | |
|---|---|---|
| | flexural strength | e-modulus |
| Example 1 | 234 MPa | 14.9 GPa |
| Example 2 | 216 MPa | 15.5 GPa |
| Example 3 | 261 MPa | 16.1 GPa |
| Example 4 | 281 MPa | 17.8 GPa |

TABLE 4c

| Flexural strengths and e-modulus (EN ISO 6872) | | | |
|---|---|---|---|
| | flexural strength | E-Modul | storage conditions |
| Example 3 | 244 MPa | 14.8 GPa | 7 days, 37° C. $H_2O$ |
| Example 3 | 216 MPa | 13.6 GPa | 7 days, 37° C. $H_2O$, thermocycling 5000 cycles |
| Example 4 | 232 MPa | 15.9 GPa | 7 days, 37° C. $H_2O$ |
| Example 4 | 219 MPa | 15.3 GPa | 7 days, 37° C. $H_2O$, thermocycling 5000 cycles |

The invention claimed is:

1. A polymerisable dental composite material, comprising
(i) 60 to 85% by weight of an inorganic filler component comprising at least one dental glass, as well as optionally at least one amorphous metal oxide,
(ii) 10 to 40% by weight of at least one monomer comprising 1,3-bis(5'-alkyl-3',8'-dioxo-2'-aza-4',7'-dioxa-decyl-9'-en)phenyl and/or 1,3-bis(5',9'-dialkyl-3',8'-dioxo-2'-aza-4',7'-dioxa-decyl-9'-en)phenyl, wherein the alkyl groups, each independently, are selected from C1 to C4 alkyl groups,
(iii) 0.01 to 5% by weight of at least one di-, tri-, tetra- or multi-functional monomer not being a urethane (meth)acrylate, comprising bis(methacryloyloxymethyl)tetrahydrocyclopentadiene, bis(acryloyloxymethyl)tetrahydrodicyclopentadiene, as well as optionally mixtures comprising at least a 3,8-/3,9-/4,8-/ 3,10-/4,10 isomer and/or cis isomer and trans isomer of the aforementioned compounds, and optionally di-, tri-, tetra- or multi-functional (meth)acrylic esters of polyethers,
(iv) 0.01 to 10% by weight of at least one initiator, of an initiator system, as well as optionally of at least one stabilizer and optionally of at least one pigment, wherein the total composition of the composite material amounts to 100% by weight.

2. The dental composite material according to claim 1, wherein
ii) the monomer comprises at least one monomer of general formula II,

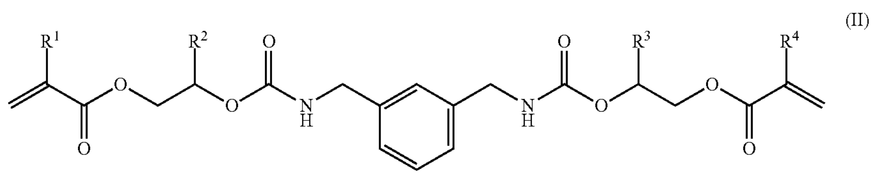

with a) $R^1$, $R^4$ equal to H and $R^2$ and $R^3$ each independently equal to C1 to C4 alkyl or b) $R^1$, $R^4$, $R^2$ and $R^3$ each independently equal to C1 to C4 alkyl.

3. The dental composite material according to claim 1, wherein the dental glass has an average particle size $d_{50}$ of 0.1 to 1.0 μm.

4. The dental composite material according to claim 1, wherein the amorphous metal oxide comprises at least one non-agglomerated amorphous metal oxide having a primary particle size of 2 to 45 nm, and the amorphous metal oxide optionally comprises precipitated silicon oxide, zirconium oxide or mixed oxides.

5. The dental composite material according to claim 1, wherein the composite material comprises as (i) inorganic filler component
(i.1) 70 to 84% by weight of at least one dental glass, and optionally
(i.2) 1 to 15% by weight amorphous metal oxide, based on the total composition.

6. The dental composite material according to claim 1, wherein (ii) further comprises a mixture of at least two different urethane (meth)acrylates, wherein the mixture comprises at least one difunctional urethane(meth)acrylate having a bivalent alicyclic group and a difunctional urethane (meth)acrylate having a bivalent alkylene group, and optionally at least one at least tetrafunctional dendritic urethane (meth)acrylate.

7. The dental composite material according to claim 1, wherein the at least one stabilizer comprises water, at least one benzophenone derivative and/or at least one phenol derivative.

8. The dental composite material according to claim 1, wherein
(ii) comprises 1,3-bis(5'-methyl-3',8'-dioxo-2'-aza-4',7'-dioxa-decyl-9'-en)phenyl and/or 1,3-bis(5',9'-dimethyl-3',8'-dioxo-2'-aza-4',7'-dioxa-decyl-9'-en)phenyl, in a mixture with at least one other urethane (meth)acrylate, and/or (iii) comprises bis(methacryloyloxymethyl)tetrahydrodicyclopentadiene, bis(acryloyloxymethyl)tetrahydrodicyclopentadiene, or a mixture of these monomers with at least one di-, tri-, tetra- or multi-functional monomer not being urethane (meth)acrylate.

9. A polymerized dental composite material obtained by polymerization of the composite material according to claim 1.

10. The polymerized dental composite material according to claim 9, having i) a flexural strength of greater than or equal to 200 MPa, dry after polymerization or 7 days, dry 23° C.+/−3° C., according to EN ISO 6872:2008, and/or ii) having a flexural strength of greater than or equal to 200 MPa, 7 days, 37° C. $H_2O$, according to EN ISO 6872:2008, and/or iii) having a flexural strength of greater than or equal to 200 MPa, 7 days, 37° C. $H_2O$, thermocycling 5000 cycles, according to EN ISO 6872:2008.

11. The polymerized dental composite material according to claim 9, wherein i) the elastic modulus amounts to greater than or equal to 12 to 21 GPa dry after polymerization or 7 days, dry 23° C.+/−3° C., according to EN ISO 6872:2008, and/or ii) the elastic modulus amounts to greater than or equal to 12 to 20 GPa, 7 days, 37° C. $H_2O$, according to EN ISO 6872:2008, and/or iii) the elastic modulus amounts to greater than or equal to 12 to 20 GPa, 7 days, 37° C. $H_2O$, thermocycling 5000 cycles, according to EN ISO 6872:2008.

12. A polymerized dental composite material comprising 60 to 85% by weight of at least one inorganic filler compound comprising at least one dental glass of an average particle size $d_{50}$ of 0.1 to 1.0 μm, as well as optionally at least one amorphous silanised metal oxide of a primary particle size of 2 to 45 nm, 10 to 40% by weight of at least one polymer being based on at least one monomer comprising (a) at least one monomer comprising 1,3-bis(5'-methyl-3',8'-dioxo-2'-aza-4',7'-dioxa-decyl-9'-en)phenyl and/or 1,3-bis(5',9'-dimethyl-3',8'-dioxo-2'-aza-4',7'-dioxa-decyl-9'-en)phenyl, (b) bis(methacryloyloxymethyl)tetrahydrodicyc lopenta diene and/or bis(acryloyloxymethyl)tetrahydrodicyc lopenta diene, and (c) optionally at least one di-urethane (meth)acrylate having a bivalent alkylene group, (d) at least one tetra- to decafunctional dendritic urethane methacrylate, and (e) optionally at least one di-, tri-, tetra- or multi-functional (meth)acrylic ester of polyethers, and 0.01 to 10% by weight of at least one pigment wherein the total composition of the composite material amounts to 100% by weight.

13. A polymerized dental composite material according to claim 9, wherein the polymerized dental composite material is present in the form of a block of material, a block of material that is present as a three-dimensional geometrical moulded body, a block material as a milling blank without an adapter, or as a milling blank with an adapter for fastening in an automated device to remove material.

14. Method of using a dental composite material according to claim 1 for the production of dental prosthetic restorations in a material-removing process or for the production of direct adhesive dental restorations.

15. Method according to claim 14 for the production of dental prosthetic restorations comprising crowns, inlay, onlays, superstructures, artificial teeth, dental bridges, dental bars, spacers, abutments or veneers.

16. Polymerized dental composite material according to claim 9 obtained by polymerization at a pressure of 50 to 300 MPa and/or elevated temperature at 90 to 150° C.

17. The polymerised dental composite material according to claim 12, wherein the polymerised dental composite material is present in the form of a block of material.

18. Method of using a dental composite material according to claim 9 for the production of dental prosthetic restorations in a material-removing process, or for the production of direct adhesive dental restorations.

19. Method of using dental composite material according to claim 12 for the production of dental prosthetic restorations in a material-removing process, or for the production of direct adhesive dental restorations.

* * * * *